United States Patent [19]
Christensen et al.

[11] 4,099,000
[45] Jul. 4, 1978

[54] PROCESS FOR PREPARING DI-7-AZIDO CEPHALOSPORIN COMPOUNDS

[75] Inventors: Burton G. Christensen, Metuchen; Ronald W. Ratcliffe, Matawan, both of N.J.

[73] Assignee: Merck & Co., Inc., Rahway, N.J.

[21] Appl. No.: 671,784

[22] Filed: Mar. 30, 1976

[51] Int. Cl.² ............................................ C07D 501/04
[52] U.S. Cl. ..................................... 544/17; 424/246; 260/306.7 C; 544/53; 544/30
[58] Field of Search ..................................... 260/243 C

[56] References Cited
FOREIGN PATENT DOCUMENTS
798,209   3/1973   Belgium ........................... 260/243 C

OTHER PUBLICATIONS

Vanderhaeghen et al., J. Med. Chem. vol. 18, 486–489 (1975).
Bose et al., JACS 4506–4508 (1968).
Guthikonda et al., JACS 7584–7585 (1974).
Cama et al., JACS 7582–7584 (1974).
Firestone et al., J. Org. Chem. vol. 39, pp. 3384–3387, 437–440 (1974).
Steinberg et al., Tetrahedron Letters pp. 3567–3570 (1974).
Ratcliffe et al., Tetrahedron Letters pp. 4653–4656 4649–4652, 4652, 4645–4648 (1973).

*Primary Examiner*—Nicholas S. Rizzo
*Attorney, Agent, or Firm*—Hesna J. Pfeiffer; Julian S. Levitt

[57] ABSTRACT

A novel total synthesis process is provided, yielding cephalosporin or penicillin compounds. The process uses as starting material a glycine ester, which first is reacted to yield a dihydrothiazine, and subsequently condensed with azidoacetyl chloride to form the cepham nucleus, then dehydrated to yield the desired 3-unsaturation. Subsequent reduction and acylation steps are analogous to known chemistry. The end products are antibacterial agents.

1 Claim, No Drawings

PROCESS FOR PREPARING DI-7-AZIDO CEPHALOSPORIN COMPOUNDS

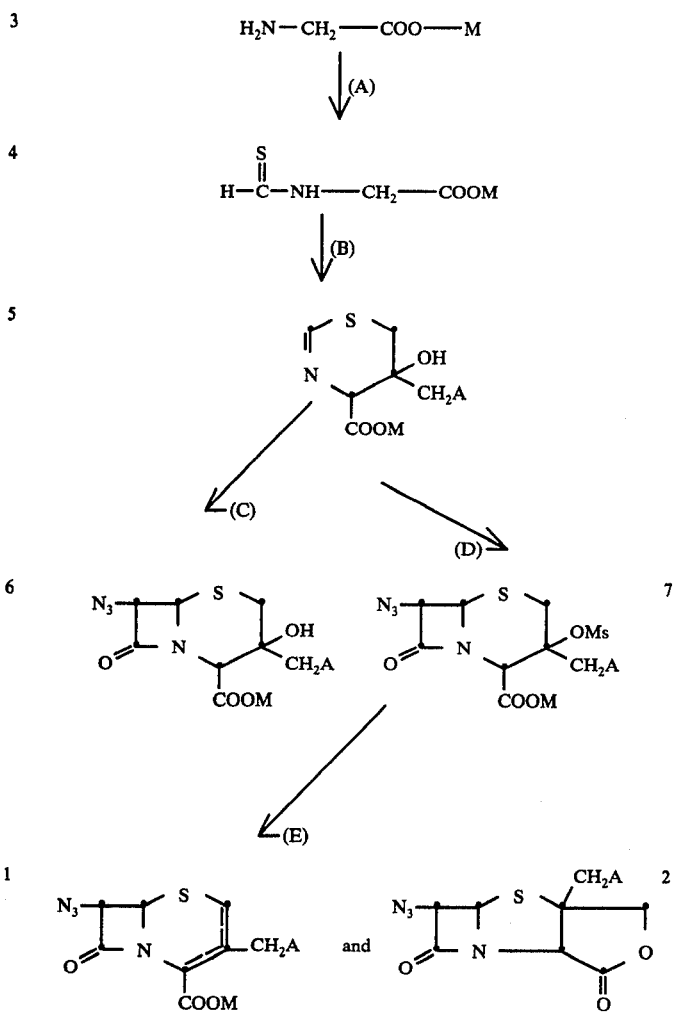

This application relates to a novel process of total synthesis of antibiotically active cephalosporin compounds.

The compounds of this invention can be represented by the following formulas:

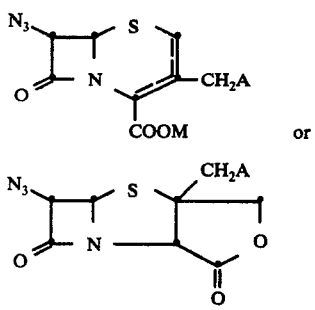

The broken line in Formula 1 indicates that either 2- or 3-unsaturation is produced. A can be hydrogen or acetoxy. The "M" indicates a carboxy protecting group, more completely defined hereinafter. The penicillin compounds of Formula 2 are novel and possess antibacterial activity.

In accordance with this invention, the following process steps are used, and can be represented schematically as follows:

In the flow sheet above, A is hydrogen or acetoxy, M is used to indicate a carboxy protecting group, preferably one which can later be easily removed to obtain the free acid form of the cephalosporin without description of the β-lactam moiety. Protecting groups suitable for this purpose are indeed well known in this art. Examples of suitable protecting ester groups that might be mentioned are those of alcohols, phenols, and the like, wherein M can be an alkyl or aralkyl group containing from 1 to about 20 carbon atoms. Thus, M can be a lower alkyl group such as methyl, ethyl or tertiary butyl, a substituted alkyl such as phthalimidomethyl, succinimidomethyl, phenacyl, substituted phenacyl such as p-bromophenacyl, a β-substituted ethyl group such as 2,2,2-trichloroethyl, 2-methylthioethyl or 2-(p-methylphenyl)ethyl, an alkenyl group such as 3-butenyl, propenyl, allyl, etc., an alkoxyalkyl group such as methoxymethyl, an aryloxyalkyl such as p-methoxyphenoxymethyl, an aralkyloxyalkyl group such as benzyloxymethyl, benzyl, or a substituted benzyl group such as p-nitrobenzyl, p-methoxybenyl, 3,5-dinitrobenzyl, 2,4,6-trimethylbenzyl or 3,5-dichloro-4-hydroxybenzyl, benzhydryl or a substituted benzhydryl group such as p-methoxybenzhydryl, and the like. Preferred blocking groups are methyl, tertiary butyl, phenacyl, p-bromophenacyl, p-nitrobenzyl, 2,2,2-trichloroethyl, p-methoxybenzyl, benzhydryl, p-methoxybenzhydryl and p-methoxyphenoxymethyl.

The compounds in the flow sheet above, labelled 5, 6, and 7 are novel intermediates useful in the preparation of active antibacterial agents.

The processes outlined in this flow sheet are described in more detail below.

Process (A) uses a glycine ester in reaction with ethyl thionoformate in an inert solvent media in the presence of hydrogen sulfide. The solvent can be carbon tetrachloride, methylene chloride, chloroform, or tetrahydrofuran. The temperature range of this step can be between 25° and −50° C., and the preferred temperature is −25° to 25° C.

Step (B) of the process comprises reacting the previously prepared thioformamido intermediate with a substituted acetone of the general formula

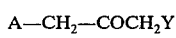

wherein A is hydrogen or acetoxy, and Y is bromo, iodo, chloro, mesyloxy, tosyloxy, or trifluoromethyl sulfonyloxy, preferably chloro or iodo. (It is most convenient to prepare the iodo form in situ by first using the chloro form, then adding sodium iodide or the like to the reacton mixture.) The reaction may be carried out at temperatures varying from 0°-50° C. in the presence of 1-5 equivalents of one or more bases such as triethylamine, an alkali metal carbonate such as potassium carbonate, phenyl lithium, an alkali metal hydride such as sodium hydride, diazobicyclononene, bis-1,8-(dimethylamino) naphthalene and the like. Following this reaction, which is more properly characterized as a series of reactions, as each reagent can be sequentially added, the corresponding dihydrothiazine is prepared.

Step (C) involves the reaction of the dihydrothiazine compound with an azidoacetyl reagent in the presence of an acid scavenger and preferably in a solvent medium at temperatures varying from −78° to 30° C. to afford the corresponding 7-azido beta-lactam compound.

The azidoacetyl reactants of particular interest have the following formula:

wherein Z is halogen, $OSO_2CF_3$ or $OSO_2CH_3$. The reaction is preferably carried out ambient temperature, for example at about 22° C., and in the presence of a sufficient amount of base such as a tertiary amine which serves as an acid scavenger and, in addition, catalyzes the cyclization of the intermediate dihydrothiazine compound. Thus, the reaction is conveniently carried out adding a solution of the azide in methylene chloride to a solution of the dihydrothiazine and a tertiary amine such as triethylamine in the same solvent; the amine being present in slight excess of the molar equivalent amount. The reaction mixture is stirred until the formation of the desired 7-azido cephalosporin compound is complete.

Step (D) prepares the 3-blocked hydroxy compound, wherein Ms is methyl sulfonyl, by reaction with methyl sulfonyl chloride.

The 7-azido intermediate is then dehydrated to yield the desired 2- or 3-unsaturated compound, Step F. This dehydration can be accomplished by reaction with a base such as triethylamine in an anhydrous inert solvent, e.g., methylene chloride, or by treatment with silica gel in an inert solvent, e.g., benzene-ethyl acetate. When the dehydrating agent is silica gel, a mixture of products which are the cephalsporin and the penicillin nucleus can be separated and isolated.

The intermediate compounds prepared can be reduced to the amine intermediates, epimerized as their p-nitrobenzylidene derivatives, thereafter acylated and the ester groups cleaved to yield the active final products. All of these steps represent processes well known in the art. Epimerization is done by preparing a Schiff's base, then cleaving to the active 7β-amino intermediate. Reduction is effected by hydrogen in the presence of a noble metal catalyst. Acylation of the amino group is accomplished using the appropriate acylating agent. The cleavage of ester groups M can be readily accomplished in accordance with processes known in this art, e.g., benzyl, or p-nitrobenzyl is removed by catalytic hydrogenation. Other common ester groups such as benzhydryl, tertiary butyl, p-methoxybenzyl and p-methoxyphenoxymethyl groups are cleaved with an acid such as trifluoroacetic acid and the 2,2,2-trichloroethyl and phenacyl groups are cleaved by reaction with zinc and acetic acid. The term "blocking group" as utilized herein is employed in the same manner and in accordance with the teaching of U.S. Pat. No. 3,697,515; the contents therein with respect to said blocking group being incorporated herein by reference.

It is noted that the processes in this application can be generally described as a shorter, more economical route than that of our prior work for total synthesis, using α-amino phosphonoacetate esters as starting materials. This work is described in Belgian Pat. No. 798,209, an equivalent of U.S. Ser. No. 336,561, filed Mar. 5, 1973, now U.S. Pat. No. 3,962,224. This prior disclosure contains detailed information as to reduction, epimerization, and acylation of the 7-azido intermediates prepared in this application, and is incorporated by reference.

In addition, the 3-methyl substituent on the cephalosporin can be converted to or readily replaced by other 3-substituents pursuant to methods well known in this art.

This invention is further illustrated by the following examples. The compounds containing one or more asymmetric carbon atoms exist as racemic compounds. These compounds can be resolved if desired by procedures known in the art. Examples 1-6 relate to the preparation of a 3-methyl cephalosporin or a penicillin; the blocking group M is p-methoxybenzyl; Examples 7-12 relate to the preparation of the same compounds where the blocking group M is p-nitrobenzyl. Examples 13-17 relate to the preparation of 3-acetoxymethyl cephalosporins, blocked by either p-nitrobenzyl or p-methoxybenzyl.

EXAMPLE 1 p-Methoxybenzyl N-thioformyl-glycinate

A mixture of p-methoxybenzyl glycinate hydrochloride (23.2 g., 0.1 mole), $H_2O$ (50 ml.), and EtOAc (150 ml.) is stirred vigorously with ice-bath cooling while an ice-cold, saturated aqueous solution of $K_2CO_3$ (25 ml.) is added. The aqueous phase is separated and extracted with more EtOAc (2 × 50 ml.). The combined EtOAc solution is dried with $MgSO_4$, filtered, evaporated in vacuo, and stripped with PhH to provide p-methoxybenzyl glycinate (17.4 g.) as a pale yellow liquid.

The above free amine (0.089 mole) in $CCl_4$ (500 ml.) is cooled to −15° C. (ice-MeOH) and the solution is stirred while ethylthionoformate (11.0 ml., 0.12 mole) is added. Hydrogen sulfide is bubbled through the resulting solution at −15° C. for 10 min. The reaction flask is securely stoppered and the mixture is stirred overnight at room temperature. The flask is opened and $N_2$ is bubbled through the mixture to dispel excess $H_2S$. The mixture is cooled in ice and filtered to remove the crude product which is washed with cold $CCl_4$ and petroleum ether and dried in vacuo to yield small white crystals (19.1 g.). The crude product is recrystallized from PhH - cyclohexane to provide p-methoxybenzyl N-thioformyl-glycinate (18.5 g.) as small white needles; mp 107°–108° C. (micro hot stage): ir ($CHCl_3$) 3.03, 5.76, 6.66, 6.93, 7.00, 7.41, 7.99, and 8.50μ; nmr ($CDCl_3$)δ3.83 (s, 3, $OCH_3$), 4.45 (d of d, 2, J=3.5 Hz and J=0.9 Hz, $NCH_2CO$), 5.20 (s, 2, $CO_2CH_2Ar$), 6.92 and 7.35 (two d's, 4, J=9 Hz, ArH), 8.13 (br m, 1, NH), and 9.55 (t of d, 1, J=4 Hz and J=0.9 Hz, HCS).

Anal. Calcd for $C_{11}H_{13}NO_3S$: C, 55.21; H, 5.47; N, 5.85; S, 13.40. Found: C, 55.09; H, 5.44; N, 5.78; S, 13.39.

EXAMPLE 2 p-Methoxybenzyl 5-hydroxy-5-methyl-5,6-dihydro-4H-1,3-thiazine-4-carboxylate

A mixture of p-methoxybenzyl N-thioformyl-glycinate (4.79 g., 20 mMols), anhydrous powdered $K_2CO_3$ (8.29 g., 60 mMols), $Me_2CO$ (50 ml.), and $ClCH_2COCH_3$ (2.0 ml., 25 mMols) is stirred in a capped flask at room temperature for 6.5 hrs. The mixture is diluted with EtOAc (100 ml.) and filtered. The filtrate is evaporated in vacuo to an oil which is taken up in $Et_2O$, washed twice with $H_2O$ and brine, dried with $MgSO_4$, filtered, and evaporated in vacuo to an orange semi-solid (5.36 g.). The crude product is dissolved in warm PhH (25 ml.) and the solution is left in a refrigerator. The pale yellow crystals of p-methoxybenzyl 5-hydroxy-5-methyl-5,6-dihydro-4H-1,3-thiazine-4-carboxylate (2.23 g.) are collected, washed with cold PhH and petroleum ether, and dried in vacuo: mp 102°–103° C. (micro hot stage); ir ($CHCl_3$) 2.97, 5.82, 6.21, 6.62, 7.97, 8.51, 9.62, and 12.04μ; nmr ($CDCl_3$) δ1.35 (s, 3, $CH_3$), 2.75 (d of d, 1, J=12 Hz and J=1Hz, SCH), 3.07 (d, 1, J=12Hz, SCH), 3,25 (br s, 1, OH), 3.82 (s, 3, $OCH_3$), 4.17 (d of d, 1, J=2Hz and J=1Hz, H4), 5.18 (s, 2, $CH_2Ar$), 6.87 and 7.33 (two d's 4, J=9Hz, ArH), and 8.23 (d, 1, J=2Hz, H2); mass spectrum m/e 295 (M+), 222, 131, and 121.

Anal. Calcd for $C_{14}H_{17}NO_4S$: C, 56.93; H, 5.80; N, 4.74; S, 10.85. Found: C, 56.98; H, 5.74; N, 4.72; S, 10.90.

EXAMPLE 3 p-Methoxybenzyl 7α-azido-3-hydroxy-3-methyl-cepham-4-carboxylate

A solution of $N_3CH_2COCl$ (210 μl, 2.4 mMol) in anhydrous $CH_2Cl_2$ (10 ml.) is added dropwise over 25 min. to a stirring solution of p-methoxybenzyl 5-hydroxy-5-methyl-5,6-dihydro-4H-1,3-thiazine-4-carboxylate (591 mg., 2 mMol) and $Et_3N$ (335 μl, 2.4 mMol) in anhydrous $CH_2Cl_2$ (20 ml.) at room temperature and under $N_2$. After 30 more min., the solution is washed twice with $H_2O$ and brine, dried with $MgSO_4$, filtered, and evaporated in vacuo to a brown foam (0.76 g.). The crude product is chromatographed on Baker silica gel (40 g., packed under 4:1 PhH - EtOAc). The products are eluted with 4:1 PhH - EtOAc; 7 ml. fractions being collected every 2 min. Fractions 21–29 are combined to provide p-methoxybenzyl 7α-azido-3-hydroxy-3-methyl-cephem-4-carboxylate (326 mg.) as a clear oil: ir (neat) 2.95, 4.76, 5.66, 5.79, 8.00 and 8.50μ; nmr ($CDCl_3$) δ1.55 (s, 3, $CH_3$), 2.50 (d, 1, J=13.5 Hz, SCH), 3.20 (d, 1, J=13.5 Hz, SCH), 3.78 (s, 3, $OCH_3$), 4.43 (s, 1, H4), 4.43 (d, 1, J=1.5 Hz, H7), 4.87 (d, 1, J=1.5 Hz, H6), 5.13 (s, 2, $CH_2Ar$), and 6.87 and 7.27 (two d's, 4, J=9Hz, ArH); mass spectrum, m/e 378 (M+) 350, 295, 229 and 121.

EXAMPLE 4 p-Methoxybenzyl 7α-azido-3-methanesulfonyloxy-3-methyl-cephem-4-carboxylate

A solution of p-methoxybenzyl 7α-azido-3-hydroxy-3-methyl-cepham-4-carboxylate (310 mg., 0.82 mMol) and $Et_3N$ (1.72 μl, 1.23 mMol) in anhydrous $CH_2Cl_2$ (4 ml.) is cooled in an ice bath under $N_2$. A solution of $MeSO_2Cl$ (83 μl, 1.07 mMol) in anhydrous $CH_2Cl_2$ (1 ml.) is added dropwise with stirring over 6 min. The resulting solution is stirred 15 more min. in the cold, then diluted with ice cold $CH_2Cl_2$ (5 ml.) and washed with ice cold $H_2O$ (5 ml.), 5% HCl (5 ml.), and 5% $NaHCO_3$ (5 ml.). The $CH_2Cl_2$ solution is dried over $MgSO_4$, filtered, and evaporated in vacuo to provide p-methoxybenzyl 7α-azido-3-methanesulfonyloxy-3-methyl-cepham-4-carboxylate (355 mg.) as a pale yellow gum: ir ($CHCl_3$) 4.78, 5.63, 5.78, 6.64, 7.43, 7.99, 8.48, and 11.08μ; nmr ($CDCl_3$) δ2.03 (s, 3, $CH_3$), 2.68 (s, 3, $SO_2CH_3$), 3.00 (d, 1, J=14Hz, SCH), 3.80 (s, 3, $OCH_3$), 3.82 (d, 1, J=14Hz, SCH), 4.47 (d, 1, J=1.3Hz, H7), 4.65 (s, 1, H4), 4.97 (d, 1, J=1.3 Hz, H6), 5.00 and 5.28 (ABq, 2, J=10.5 Hz, $CH_2Ar$), and 6.87 and 7.33 (two d's, 4, J=9Hz, ArH).

EXAMPLE 5 p-Methoxybenzyl 7α-azido-3-methyl-ceph-3-em-4-carboxylate and p-methoxybenzyl 7α-azido-3-methyl-ceph-2-em-4-carboxylate A. A solution of p-methoxybenzyl 7α-azido-3-methanesulfonyloxy-3-methyl-cepham-4-carboxylate (100 mg., 0.22 mMol) and $Et_3N$ (31μl, 0.22 mMol) is kept at 37° C. for 8 hrs. The solution is diluted with PhH to 6 ml., washed with $H_2O$ (3 ml.), 5% HCl (2 ml.), and 5% $NaHCO_3$ (3 ml.), dried with $MgSO_4$, filtered, and evaporated in vacuo to an orange oil (73 mg.). The product is a 2:1 mixture of p-methoxybenzyl 7α-azido-3-methyl-ceph-3-em-4-carboxylate and p-methoxybenzyl 7α-azido-3-methyl-ceph-2-em-4-carboxylate. The ceph-3-em isomer shows: ir (neat) 4.77, 5.64, 5.81, 6.61, 7.21, 7.34, 7.67, 8.04, 8.26, 8.47, 8.89, 9.62, and 12.03μ; nmr ($CDCl_3$) δ2.10 (s, 3, $CH_3$), 3.10 and 3.50 (ABq, 2, J=18Hz, $SCH_2$), 3.82 (s, 3, $OCH_3$), 4.47 (d, 1, J=1.5Hz, H7), 4.57 (d, 1, J=1.5Hz, H6), 5.23 (s, 2, $CH_2Ar$), and 6.88 and 7.33 (two d's, 4, J=9Hz, ArH). The ceph-2-em isomer shows nmr ($CDCl_3$) δ1.82 (m, 3, $CH_3$), 4.48 (d, 1, J=1.5Hz, H7), 4.72 (m, 1, H4), 4.88 (d, 1, J=1.5Hz, H6), 5.10 (s, 2, $CH_2Ar$), and 5.87 (m, 1, SCH).

B. A solution of p-methoxybenzyl 7α-azido-3-methanesulfonyloxy-3-methyl-cepham-4-carboxylate (57 mg.) in $CHCl_3$ (0.5 ml.) is treated with 1,5-diazabicylo [4,3,0]non-5-ene (25 μl) and kept at 37° C. for 3 min. Acetic acid (25 μl) is added and the solution is diluted with PhH, washed with $H_2O$, 5% $NaHCO_3$, 5% HCl, and 5% NaHCO₃, dried with MgSO₄, filtered, and evaporated in vacuo to a yellow oil (39 mg.). The nmr spectrum of this material shows a 2:1 mixture of ceph-3-em to ceph-2-em.

EXAMPLE 6 p-Methoxybenzyl 7α-azido-3-methyl-ceph-3-em-4-carboxylate and 6α-azido-2-methyl-2-hydroxymethyl-penam-3-carboxylic acid lactone A mixture of p-methoxybenzyl 7α-azido-3-methanesulfonyloxy-3-methyl-cepham-4-carboxylate (210 mg., 0.46 mMol), EM silica gel 60 (2.5 g.), and 3:1 PhH-EtOAc (5 ml.) is stirred in a capped flask at room temperature for 93 hrs. The mixture is diluted with EtOAc and filtered. The silica gel is washed with more EtOAc. The filtrate and washings are combined, washed with 5% NaHCO₃ and brine, dried with MgSO₄, filtered, and evaporated in vacuo to a pale yellow oil (158 mg.). The material is purified by plc on a 1000μ × 20 × 20 cm silica gel GF plate using 9:1 PhH-EtOAc as developing solvent. Two major uv visible bands are removed and eluted with EtOAc to yield the products. Band A ($R_f$ 0.47) provides p-methoxybenzyl 7α-azido-3-methyl-ceph-3-em-4-carboxylate (51 mg.) as an oil. Band B ($R_f$ 0.26) yields 6α-azido-2-methyl-2-hydroxymethyl-penam-3-carboxylic acid lactone (27 mg.) as an oil which crystallizes from CHCl₃: mp 164°–166° C. (micro hot stage); ir (Nujol) 4.76, 5.57, 5.67, 7.74, 8.32, and 9.79μ; nmr (100 MHz, DMSO-d₆) δ1.59 (s, 3, CH₃), 4.30 and 4.52 (ABq, 2, J=10Hz, CH₂O), 5.20 (d, 1, J=1.8Hz, H5 or H6), 5.28 (s, 1, H3) and 5.29 (d, 1, J=1.8Hz, H6 or H5); mass spectrum, m/e 240 (M+), 212, and 157.

Anal. Calcd for $C_8H_8N_4O_3S$: C, 40.00; H, 3.35; N, 23.32; S, 13.34. Found: C, 39.98; H, 3.22; N, 23.20; S, 13.63.

EXAMPLE 7 p-Nitrobenzyl N-thioformyl-glycinate p-Nitrobenzyl glycinate hydrobromide (2.91 g., 10mMol) is suspended in H₂O (5 ml.) and layered with EtOAc (15 ml.) The mixture is cooled in ice and stirred while ice-cold, saturated aqueous K₂CO₃ (2.5 ml.) is added. The layers are separated and the aqueous portion is extracted with more EtOAc (3 × 5 ml.). The combined EtOAc solution is washed with H₂O and brine, dried with Na₂SO₄, filtered, and evaporated in vacuo to an off-white solid (1.81 g.). Recrystallization from Et₂O yields p-nitrobenzyl glycinate as small, off-white needles.

A solution of p-nitrobenzyl glycinate (350 mg., 1.67 mMol) in CHCl₃ (9 ml.) is cooled to ca. −10° C. (ice-MeOH) and stirred. Ethyl thionoformate (209 μl, 2.27 mMol) is added and H₂S is bubbled through the resulting solution at ca −10° C. for 10 min. The reaction flask is securely stoppered at −10° C., and the reaction mixture is stirred overnight at room temperature. The flask is opened and N₂ is bubbled through the mixture to expel excess H₂S. The mixture is filtered to remove a small amount (38 mg.) of an insoluble, off-white solid. Evaporation of the filtrate in vacuo leaves a pale yellow oil (385 mg.) which crystallizes on standing. This material is dissolved in warm PhH and the solution is cooled with scratching. The resulting precipitate of p-nitrobenzyl N-thioformyl-glycinate is collected, washed with petroleum ether, and dried in vacuo to a pale yellow powder (313 mg.): mp 92°–94° C. (micro hot stage); nmr (DMSO-d₆) δ4.52 (d, 2, J=5.5Hz, NCH₂CO₂), 5.33 (s, 2, CH₂Ar), 7.67 and 8.23 (two d's, 4, J=9Hz, ArH), 9.45 (d, 1, J=6Hz, HCS), and 10.57 (br m, 1, NH); ir (CHCl₃) 2.91, 5.71, 6.58, 7.03, 7.44 and 8.44μ; mass spectrum, m/e 254 (M+), 221, 136, and 118.

Anal. Calcd. for $C_{10}H_{10}N_2O_4S$: C, 47.24; H, 3.96; N, 11.02; S, 12.61. Found: C, 47.35; H, 3.96; N, 10.80; S, 12.22.

EXAMPLE 8 p-Nitrobenzyl 5-hydroxy-5-methyl-5,6-dihydro-4H-1,3-thiazine-4-carboxylate

A mixture of p-nitrobenzyl N-thioformyl-glycinate (508 mg., 2 mMol), anhydrous powdered K₂CO₃ (829 mg., 6 mMol), Me₂CO (5 ml.), and ClCH₂COCH₃ (201 μl, 2.5 mMol) is stirred in a capped flask at room temperature for 2.5 hrs. The mixture is diluted with EtOAc (10 ml.) and filtered. The filtrate is evaporated in vacuo. The residue is taken up in EtOAc, washed twice with H₂O and brine, dried with MgSO₄, filtered, evaporated in vacuo, and stripped with PhH to an amber oil (648 mg.).

The crude product is chromatographed on Baker silica gel (30 g., packed under 1:1 PhH-EtOAc). The product is eluted with 1:1 PhH-EtOAc; 3 ml. fractions being collected every 1.75 mins. Fractions 16–19 are combined to provide p-nitrobenzyl 5-hydroxy-5-methyl-5,6-dihydro-4H-1,3-thiazine-4-carboxylate (240 mg.) as a yellow oil: ir (neat) 3.2, 5.78, 6.24, 7.43, and 8.43μ; nmr (CDCl₃) δ1.42 (s, 3, CH₃), 2.82 (d of d, 1, J=12.5Hz and J=1Hz, SCH), 3.17 (d, 1, J=12.5Hz, SCH), 3.50 (br s, 1, OH), 4.33 (d of d, 1, J=2Hz and J=1Hz, H4), 5.35 (s, 2, CH₂Ar), 7.53 and 8.18 (two d's, J=9Hz, ArH), and 8.27 (d, 1, J=2Hz, H2); mass spectrum, m/e 310 (M+), 277, 221, 174, 157 and 136.

EXAMPLE 9 p-Nitrobenzyl 7α-azido-3-hydroxy-3-methyl-cepham-4-carboxylate p-Nitrobenzyl 5-hydroxy-5-methyl-5,6-dihydro-4H-1,3-thiazine-4-carboxylate (240 mg., 0.77 mMol) and Et₃N (130 μl, 0.93 mMol) in anhydrous CH₂Cl₂ (10 ml.) is stirred under N₂ at room temperature while a solution of N₃CH₂COCl (82 μl, 0.93 mMol) in CH₂Cl₂ (5 ml.) is added dropwise over 40 min. After stirring 30 more min. at room temperature, the solution is washed twice with H₂O and brine, dried with MgSO₄, filtered, and evaporated in vacuo to an orange oil (309 mg.)

The crude product is chromatographed on Baker silica gel (15 g., packed under 4:1 PhH-EtOAc). The product is eluted with 4:1 PhH-EtOAc; 4 ml. fractions being collected every 1.25 min. Fractions 16-27 are combined to yield p-nitrobenzyl 7α-azido-3-hydroxy-3-methyl-cepham-4-carboxylate (138 mg.) as a clear gum: ir (CHCl₃) 2.97, 4.77, 5.63, 5.75, 6.58, 7.41, and 8.50μ; nmr (CDCl₃) δ1.63 (s, 3, CH₃), 2.58 (d, 1, J=14Hz, SCH), 3.25 (d, 1, J=14Hz, SCH), 3.37 (s, 1, OH), 4.57 (d, 1, J=1.3Hz, H7), 4.58 (s, 1, H4), 4.93 (d, 1, J=1.3Hz, H6), 5.33 (s, 2, CH₂Ar), and 7.55, 8.22 (two d's, 4, J=9Hz, ArH); mass spectrum, m/e 365 (M+-28), 310, 277, 229, 221, 174, 157 and 136.

EXAMPLE 10 p-Nitrobenzyl 7α-azido-3-methanesulfonyloxy-3-methyl cepham-4-carboxylate

A solution of $CH_3SO_2Cl$ (34 μl, 0.44 mMol) in anhydrous $CH_2Cl_2$ (0.5 ml.) is added dropwise over 4 min. to an ice-cold, stirring solution of p-nitrobenzyl 7α-azido-3-hydroxy-3-methyl-cepham-4-carboxylate (135 mg., 0.34 mMol) and $Et_3N$ (71 μl, 0.51 mMol) in anhydrous $CH_2Cl_2$ (2 ml.). After stirring 15 more min. in the cold, the reaction mixture is diluted with cold $CH_2Cl_2$ (2 ml.), washed with ice-cold $H_2O$ (2 ml.), ice-cold 5% HCl (2 ml.), and ice-cold 5% $NaHCO_3$ (2 ml.), dried over $MgSO_4$, and filtered. Evaporation of the solvent in vacuo gives p-nitrobenzyl 7α-azido-3-methanesulfonyloxy-3-methyl-cepham-4-carboxylate (156 mg.) as a pale yellow oil: ir ($CHCl_3$) 4.76, 5.62, 5.75, 6.57, 7.40, 8.47, and 11.1μ; nmr ($CDCl_3$) δ2.10 (s, 3, $CH_3$), 2.93 (s, 3, $SO_2CH_3$), 3.02 (d, 1, J=14Hz, SCH), 3.87 (d, 1, J=14Hz, SCH), 4.53 (d, 1, J=1.2Hz, H7), 4.80 (s, 1, H4), 4.97 (d, 1, J=1.2Hz, H6), 5.35 (s, 2, $CH_2Ar$), and 7.60, 8.28 (two d's 4, J=8.7Hz, ArH).

EXAMPLE 11 p-Nitrobenzyl 7α-azido-3-methyl-ceph-3-em-4-carboxylate and p-Nitrobenzyl 7α-azido-3-methyl-ceph-2-em-4-carboxylate A solution of p-nitrobenzyl 7α-azido-3-methanesulfonyloxy-3-methyl-cepham-4-carboxylate (26 mg., 0.055 mMol) and $Et_3N$ (8μl, 0.057 mMol) in $CHCl_3$ (0.4 ml.) is kept at 37° C. for 2 hrs. The solution is diluted with PhH, washed with $H_2O$, 5% HCl, and 5% $NaHCO_3$, dried with $MgSO_4$, filtered, and evaporated in vacuo to an oil (19 mg.). The nmr spectrum of this material shows a 3:1 mixture of p-nitrobenzyl 7α-azido-3-methyl-ceph-3-em-4-carboxylate and p-nitrobenzyl 7α-azido-3-methyl-ceph-2-em-4α-carboxylate. The ceph-3-em isomer has the following resonances: nmr ($CDCl_3$) δ2.18 (s, 3, $CH_3$), 3.18 and 3.55 (ABq, 2, J=17.5 Hz, $SCH_2$), 4.52 (d, 1, J=1.5Hz, H7), 4.62 (d, 1, J=1.5Hz, H6), 5.37 (s, 2, $CH_2Ar$), and 7.57, 8.22 (two d's, 4, J=9Hz, ArH).

EXAMPLE 12 p-Nitrobenzyl 7α-azido-3-methyl-ceph-3-em-4-carboxylate and 6α-azido-2-methyl-2-hydroxymethyl-penam-3-carboxylic acid lactone A mixture of p-nitrobenzyl 7α-azido-3-methanesulfonyloxy-3-methyl-cepham-4-carboxylate (128 mg.), EM silica gel (1.3 g.), and 3:1 PhH-EtOAc (3.5 ml.) is stirred at room temperature in a capped flask for 12 hrs. The mixture is diluted with EtOAc and filtered; the silica gel being washed with more EtOAc. The combined filtrate and washings are washed with 5% $NaHCO_3$ and brine, dried with $MgSO_4$, filtered, evaporated in vacuo, and stripped with PhH to provide an oil (99 mg.). The nmr spectrum of this material shows ca. 35% conversion to products.

The above oil is dissolved in 3:1 PhH-EtOAc (3 ml.) and stirred with EM silica gel (1.3 g.) in a capped flask at room temperature for 26 hrs. Work-up as above provides an oil (85 mg.) which is shown by nmr to be a 5:2:2 mixture of p-nitrobenzyl 7α-azido-3-methyl-ceph-3-em-4-carboxylate, 6α-azido-2-methyl-2-hydroxymethyl-penam-3-carboxylic acid lactone, and starting material respectively.

EXAMPLE 13 p-Nitrobenzyl 5-hydroxy-5-acetoxymethyl-5,6-dihydro-4H-1,3-thiazine-4-carboxylate A mixture of 1-acetoxy-3-chloro-2-propanone (1.51 g., 10 mMol), NaI (1.50 g., 10 mMol), and acetone (20 ml.) is stirred at room temperature for 5 min. p-Nitrobenzyl N-thioformyl-glycinate (2.54 g., 10 mMol) and $Et_3N$ (1.39 g., 10 mMol) are then added and the resulting mixture is stirred at room temperature for 30 min. Anhydrous, powdered $K_2CO_3$ (2.76 g., 20 mMol) is added and stirring is continued for a further 60 min. The mixture is diluted with EtOAc (50 ml.) and filtered. The filtrate is evaporated in vacuo. The residue is taken up in EtOAc, washed twice with $H_2O$ and brine, dried with $MgSO_4$, filtered, and evaporated in vacuo to an oil.

The crude product is chromatographed on a column of Baker silica gel. Elution with 1:1 PhH-EtOAc provides p-nitrobenzyl 5-hydroxy-5-acetoxymethyl-5,6-dihydro-4H-1,3-thiazine-4-carboxylate.

EXAMPLE 14 p-Nitrobenzyl 7α-azido-3-hydroxy-3-acetoxymethyl-cepham-4-carboxylate p-Nitrobenzyl 5-hydroxy-5-acetoxymethyl-5,6-dihydro-4H-1,3-thiazine-4-carboxylate (1.27 g., 3.45 mMol) and $Et_3N$ (0.58 ml., 4.16 mMol) in anhydrous $CH_2Cl_2$ (50 ml.) is stirred under a $N_2$ atomsphere at room temperature while a solution of $N_3CH_2COCl$ (0.36 ml., 4.13 mMol) in anhydrous $CH_2Cl_2$ (20 ml.) is added dropwise over 90 min. After stirring 30 more min., the solution is washed twice with $H_2O$ and brine, dried with $MgSO_4$, filtered, and evaporated in vacuo. The residual oil us chromatographed on a column of Baker silica gel. Elution with 3:1 PhH-EtOAc yields p-nitrobenzyl 7α-azido-3-hydroxy-3-acetoxymethyl-cepham-4-carboxylate.

EXAMPLE 15 p-Nitrobenzyl 7α-azido-3-methanesulfonyloxy-3-acetoxymethyl-cepham-4-carboxylate A solution of methanesulfonyl chloride (0.145 ml, 1.87 mMol) in anhydrous $CH_2Cl_2$ (2 ml.) is added dropwise over 10 min. to an ice-cold, stirring solution of p-nitrobenzyl 7α-azido-3-hydroxy-3-acetoxymethyl-cepham-4-carboxylate (0.65 g., 1.44 mMol) and $Et_3N$ (0.30 ml, 2.16 mMol) in anhydrous $CH_2Cl_2$ (10 ml.). After stirring 15 more min. in the cold, the solution is diluted with ice-cold $CH_2Cl_2$ (10 ml.), washed with ice-cold $H_2O$ (10 ml.), ice-cold 5% HCl (10 ml.), and ice-cold 5% $NaHCO_3$ (10 ml.), dried with $MgSO_4$, and filtered. Evaporation of the solvent in vacuo leaves p-nitrobenzyl 7α-azido-3-methanesulfonyloxy-3-acetoxymethyl-cepham-4-carboxylate.

EXAMPLE 16 p-Nitrobenzyl 7α-azido-3-acetoxymethyl-ceph-3-em-4-carboxylate

A mixture of p-nitrobenzyl 7α-azido-3-methanesulfonyloxy-3-acetoxymethyl-cepham-4-carboxylate (0.72 g.), EM silica gel 60 (7.20 g.), and 3:1 PhH-EtOAc (20 ml.) is stirred in a stoppered flask for 4 days at room temperature. The mixture is filtered through a sintered glass funnel to remove the silica gel, which is washed with several portions of EtOAc. Evaporation of the filtrate and washings leaves an oil. This material is chromatographed on Baker silica gel using 9:1 φH-EtOAc as an eluting solvent, to provide p-nitrobenzyl 7α-azido-3-acetoxymethyl-ceph-3-em-4-carboxylate.

EXAMPLE 17 p-Methoxybenzyl 7α-azido-3-acetoxymethyl-ceph-3-em-4-carboxylate

By employing procedures similar to those described in Examples 13-16 and by utlizing p-methoxybenzyl N-thioformyl-glycinate as starting material, p-methoxybenzyl 7α-azido-3-acetoxymethyl-ceph-3-em-4-carboxylate is obtained.

What is claimed is:

1. The process of preparing a dl-7-azido cephalosporin of the formula

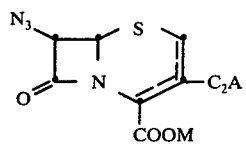

wherein A is hydrogen or acetoxy and M is benzyl, y-methoxy benzyl, or p-nitrobenzyl, which comprises reacting a compound of the formula

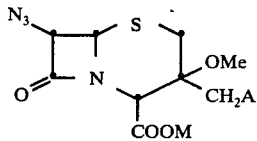

wherein A and M are as defined, and Ms indicates methyl sulfonyl, with
(a) silica gel at room temperature for from about 12 hours to about 96 hours, in an anhydrous inert solvent; or
(b) an equimolar amount of triethylamine at 37° C. for from about 2 to about 8 hours in an anhydrous inert solvent;
and recovering the product thereby produced.

* * * * *